United States Patent [19]

Orth et al.

[11] Patent Number: 4,865,620
[45] Date of Patent: Sep. 12, 1989

[54] HAIR DYE COMPOSITION

[75] Inventors: Winfried Orth, Hassloch/Pfalz; Wolfgang Weiss, Neckarhausen; Hans W. Kleffner, Battenberg, all of Fed. Rep. of Germany

[73] Assignee: Ruetgerswerke Aktiengesellschaft, Frankfurt am Main, Fed. Rep. of Germany

[21] Appl. No.: 239,401

[22] Filed: Sep. 1, 1988

[30] Foreign Application Priority Data

Sep. 18, 1987 [DE] Fed. Rep. of Germany ....... 3731396
Feb. 11, 1988 [DE] Fed. Rep. of Germany ....... 3804221

[51] Int. Cl.$^4$ .................... C07D 401/00; A61K 7/13
[52] U.S. Cl. ........................................ 8/420; 546/281; 8/408; 8/409
[58] Field of Search ................. 548/531; 546/281; 8/408, 409, 423

[56] References Cited

U.S. PATENT DOCUMENTS 3,873,545  3/1975  Osselaere et al. ................... 546/281
4,517,185  5/1985  Barth et al. ......................... 546/281

Primary Examiner—Paul Lieberman
Assistant Examiner—John F. McNally
Attorney, Agent, or Firm—Beveridge, DeGrandi & Weilacher

[57] ABSTRACT

Hair dye compositions based on oxidation hair dyes which contain developer components, coupling components and oxidation components, characterized in that they contain one or more aminopyrrole derivatives of the formula:

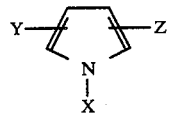

11 Claims, No Drawings

HAIR DYE COMPOSITION

INTRODUCTION AND BACKGROUND

The invention relates to hair dyes based on oxidation dyes in combination with appropriate developer compounds. The coloring of hair takes place, as is known in the art, by means of the reaction of the developer substances with so-called coupler substances or tinters in an alkaline medium in the presence of a suitable oxidation agent. These oxidation colors play a significant role in the field of hair cosmetics because of the generally intensive colors produced thereby which have very good fastness properties and because of the great degree of variation in the color tones obtainable thereby.

Known coupler or tinting components are m-phenylene diamine derivatives, phenols, naphthols or resorcinol derivatives. However, since all these products are not safe from a toxicologic and dermatological viewpoint, attempts have been made to switch to the safer heterocyclic compounds.

Thus, the use of the following as coupler substances is known:
- 2,3- and 2,5-diaminopyridine from DE-PS (W. German) No. 11 42 045,
- 2,5-diaminopyridine from DD-PS No. (East German) 57 402,
- bis-aminopyridines from EP No.0,008,079 Bl,
- dihydroxypyridines from U.S. Pat. No. 1,571,570,
- hydroxy and alkoxypyridine amines from FR Nos. 1,397,551 and FR 1,398,198,
- pyridyl aminobenzenes and bispyridyl amines from FR No. 1,401,469,
- nitropyridine amines from EP-A No. 0,137,524 or
- dinitropyridine amines from EP-A No. 0,193,656.

In spite of the numerous existing hair dyes, there is still a need for better coupler compounds, partially because some of these coupling components are not sufficiently resistant to atmospheric oxygen or can not be combined with tensides (surfactants) of the various groups and partially in order to be able to fill the palette of color shades even better with intensive colors having very good fastness properties. In particular, there is a need for red tones since it is desirable to do without nitro-p-phenylene diamine, which has been used for this purpose up to the present, for toxicologic reasons.

Prior to this invention, therefore, there was the problem of developing hair dyes based on oxidation dyes which result in intensive colors having very good fastness properties, especially in the area of the red tones, and whose coupler or tinting components are quite resistant to atmospheric oxygen so that they can also be used in small amounts in neutral or salt form.

SUMMARY OF THE INVENTION

An object of the present invention is to provide hair dye compositions based on oxidation hair dyes which contain developer components, coupling components and oxidation components, wherein as the coupling component there is used one or more aminopyrrolle derivaties of the formula I

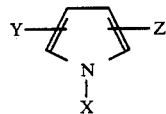

(I)

in which X represents hydrogen, a methyl or ethyl group, Y is in position 4 or 5 in the ring and represents hydrogen, an amino, hydroxy or methyl group, an alkoxy group with 1 to 3 C atoms or Y may be a second group Z, and Z is in position 2 or 3 on the ring and represents a group of the formula II $$-(C_aH_{2n})-NH-R \qquad (II)$$

in which n represents a number from 1 to 3 and R represents an N-methylpyrrole or N-ethylpyrrole, pyrrole, pyridine, piperidine, pyrimidine or morpholine group which is unsubstituted or substituted by amine-, methoxy- or ethoxy-, or amine- and methoxy- or ethoxy- at any position.

A further object of the invention is to provide compositions containing other coupling components in addition to the alkylaminopyrrole derivatives.

Still a further object of the present invention resides in certain novel compounds; namely,
- 2-(5'-amino-2'methoxy-6'-ethylene aminopyridine)-1H-pyrrole;
- 2-(5'-amino-2'-methoxy-6'-ethylene aminopyridine)-1H-methyl-pyrole,
- 2-(3'-amino-6'-ethylene aminopyridine)-1H-pyrrole, and
- 2-(3'amino-6'-ethylene aminopyridine)-1H-1-methyl-pyrrole.

DETAILED DESCRIPTION OF THE INVENTION

It has now been found that aminopyrrole derivatives of the formula I

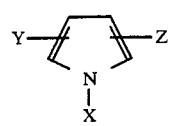

(I)

in which X represents hydrogen, a methyl or ethyl group, Y is in position 4 or 5 in the ring and represents hydrogen, an amino, hydroxy or methyl group, an alkoxy group with 1 to 3 C atoms or Y represents a second group Z, and Z is in position 2 or 3 in the ring and signifies a group of the formula II $$-(C_nH_{2n})-NH-R \qquad (II)$$

in which n represents a number from 1 to 3 and R represents an N-methylpyrrole or N-ethylpyrrole, pyrrole, pyridine, piperidine, pyrimidine or morpholine group which is unsubstituted or amine-, methoxy- or ethoxy-, or amine- and methoxy- or ethoxy-substituted at any position, in combination with appropriate developer components and oxidation agents make good coupler or tinting components which meet the above-mentioned requirements, even if they are used in slight amounts. It is especially surprising that these aminopyrrole derivatives result in a preferred manner in brilliant red tones.

Different color variants can be obtained by varying the substituents on the pyrrole ring and on the amino group of the compounds used in accordance with the invention. It is thus possible with these means to set almost all color variants with one oxidation color system by mixing different tinting components. Thus, the hair dyes of the invention constitute an enrichment of the hair cosmetics art.

Coupler components in accordance with the invention to be used in oxidation dye systems are derivatives of pyrrole, N-methylpyrrole or N-ethylpyrrole which comprise a group of the general formula —$(C_nH_{2n})$—NH—R in position 2 or 3 on the pyrrole ring. The remaining pyrrole ring can be unsubstituted or substituted in position 4 or 5 by a methyl, methoxy, ethoxy, propoxy, hydroxy or amino group or by a second alkylamino group of the general formula —$(C_nH_{2n})$—NH—R.

The amino group is substituted with a pyrrole, N-methylpyrrole, N-ethylpyrrole, pyridine, piperidine, pyrimidine or morpholine group which is unsubstituted or substituted at any position.

The substituents of these heterocycles can be either an amino group or a methoxy or ethoxy group as well as an amino group and a methoxy or ethoxy group.

The aminopyrrole derivatives of the invention can be prepared in a known manner by reduction of the corresponding nitropyrrole derivatives. Examples for corresponding nitropyrrole derivatives as well as examples for a method of preparing them are known from DE-A-No. 33 34 029.

The coupling components of the invention can be used alone or, in order to set desired color nuances, in a mixture with each other or with other known tinting or coupler components.

The following can be cited as examples for developer components to be used in the hair dyes of the invention: Primary aromatic amines with a further functional group in p-position such as
p-phenylene diamine,
alkylamino-p-phenylene diamines,
p-toluylene diamine,
p-aminophenol,
N-methyl-p-phenylene diamine,
N,N-dimethyl-p-phenylene diamine,
N,N-diethyl-2-methyl-p-phenylene diamine,
N-ethyl-N-hydroxyethyl-p-phenylene diamine,
Chloro-p-phenylene diamine,
N,N-bis-hydroxyethylamino-p-phenylene diamine,
methoxy-p-phenylene diamine,
2,6-dichloro-p-phenylene diamine,
2-chloro-6-bromo-p-phenylene diamine,
2-chloro-6-methyl-p-phenylene diamine,
6-methoxy-3-methyl-p-phenylene diamine,
other compounds of the type cited which also contain one or more functional groups such as OH groups, $NH_2$ groups, NHR groups, $NR_2$ groups, in which instance R represents an alkyl or hydroxyalkyl group with 1-4 carbon atoms.

Further examples are:
heterocyclic hydrazone derivatives such as
1-methylpyrrolidone-(2)-hydrazone,
4-aminopyrazolone derivatives such as
4-amino-1-phenyl-3-carbamoyl pyrazolone-5,
N-butyl-N-sulfobutyl-p-phenylene diamine,
tetraaminopyrimidines such as
2,4,5,6-tetraaminopyrimidine,
4,5-diamino-2,6-bismethylaminopyridine,
2,5-diamino-4-diethylamino-6-methylaminopyrimidine,
2,4,5-triamino-6-dimethylaminopyrimidine,
2,4,5-triamino-6-piperidinopyrimidine,
2,4,5-triamino-6-anilinopyrimidine,
2,4,5-triamino-6-morpholinopyrimidine,
2,4,5-triamino-6- -hydroxyethylaminopyrimidine,
but also pyridine derivatives such as e.g. 2,5-diaminopyridine or
2,5-diamino-4-methylpyridine.

The oxidative coupling, that is, the development of the coloring, could basically also take place by means of atmospheric oxygen as in the case of other oxidation hair dyes. However, the reaction speed is too low for practical application and the development of color on the hair too slow. Therefore, chemical oxidation means are preferably used. Such chemical oxdation means are potentially and in particular hydrogen peroxide or its addition products with urea, melamine and sodium borate as well as mixtures of such hydrogen peroxide addition compounds with potassium peroxydisulfate.

The hair dyes of the invention which contain the coupling and developer component can be prepared for commercial use in appropriate cosmetic preparations such as creams, emulsions, gels or also simple solutions. These are generally aqueous. It is occasionally necessary to this end to heat the solutions up to 100° C. in order to bring the components into solution, if necessary with the aid of a solutizing agent. The concentration of the coupling components is between 0.01-2% by weight and of developer component between 0.1-5% by wt. in usable products. The components are mixed with the other components customarily included in such preparations for the manufacture of the cosmetic preparation.

Such additional components are e.g. ammonium hydroxide, wetting agents or emulsifying agents of the anionic or nonionogenic type such as alkylbenzene sulfonates, fatty alcohol sulfonates, fatty alcohol ether sulfates, amine oxides, alkylsulfonates, fatty acid alkanol amides, alkylphenoloxalkylates and addition products of ethylene oxide to fatty alcohol, reducing agents such as sodium sulfite, sodium dithionite, thioglycolic acid or ascorbic acid, thickening agents such as methyl cellulose, higher fatty alcohols, fatty acids, moreover perfumed oils and hair conditioners or tonics such as pantothenic acid and cholesterol.

Shortly before they are used, these hair dye compositions are mixed with a solution of one of the cited oxidation agents in a customary manner and the mixture obtained in this manner is applied to the hair in the usual manner. The application temperatures range from 30° to 40° C. After an exposure time of approximately 30 minutes, the hair dye is removed from the hair to be dyed by rinsing. Then the hair is washed with a mild shampoo and dried.

The following examples serve to illustrate the present invention.

EXAMPLES 1 to 5

Dyeing tests were performed with hair dyes of the following base composition:
2% by wt. 30% fatty acid amine oxide solution,
0.5% by wt. sodium dithionite,
10% by wt. 25% ammonium hydroxide,
0.5% by wt. coupling component in accordance with the invention,
1% by wt. phenylene diamine, 86% by wt. water.
100 ml of the hair dye were mixed with 10 ml hydrogen peroxide solution (6%). Hair strands of natural hair were immersed into these mixtures and the dyeing solution allowed to act 30 minutes at 35° C. Then the strands were rinsed well, dried and evaluated as to their color.

EXAMPLE 1

2-(5'-1'methylpyrrole-methylene amino)-5-methylpyrrole

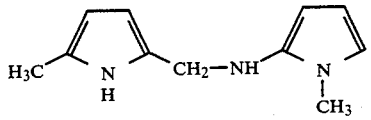

Color: reddish brown

EXAMPLE 2

2-(5'-amino-2'-methoxy-6'-ethylene aminopyridine)-1H-pyrrole

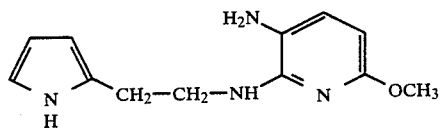

Color: red - reddish violet

EXAMPLE 3

2-(3'-amino-6'-ethylene aminopyridine)-1H-pyrrole

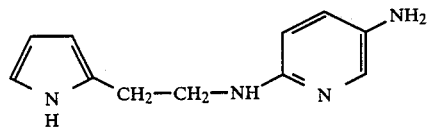

Color: red - reddish violet

EXAMPLE 4

2-(5'-amino-2'-methoxy-6'-ethylene aminopyridine)-1-methyl-1H-pyrrole

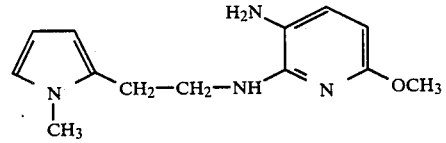

Color: raspberry red

EXAMPLE 5

2-(3'-amino-6'-ethylene aminopyridine)-1-methyl-1H-pyrrole

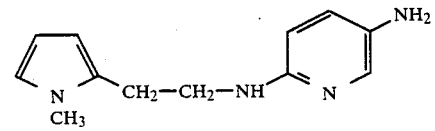

Color: raspberry red

EXAMPLE 6

2-(5'-amino-2'-methoxy-6'-ethylene aminopyridine)-1H-1-methylpyrrole 69 g (0.25 mole) 2-(2'-methoxy-5'-nitro-6'-ethylene aminopyridine)-1H-methyl-pyrrole are reduced with 25 g Raney nickel as catalyst 20 h at 65° C. and 6–7 bar H2 pressure in 1000 ml methanol as solvent. The reaction mixture is compounded with 3000 ml water, the precipitated amine is filtered off by suction, then washed several times with water and dried at 60° C. in a vacuum.

The raw product exhibits a violet color. This color originates from a red byproduct which is present in only a very small amount.

A purification by recrystallization is not possible.
Yield: 27 g=44%
Fp: 93°–94° C.
Elementary analysis:
Calculated: C 63.4 H 7.3 N 22.7%
Found: C 62.8 H 7.3 N 22.6%

EXAMPLE 7

2-(5'-amino-2'-methoxy-6'-ethylene amino)-1H-pyrrole 65.5 g 2-(2'-methoxy-5'-nitro-6'-ethylene amino)-1H-pyrrole are reduced in an analogous manner with example 6.

25 g of a light violet product are obtained.
Fp: 98°–99° C.

EXAMPLE 8

2-(3'-amino-6'-ethylene aminopyridine)-1H-pyrrole

In a manner analogous to example 6 52.25 g 2-(3'-nitro-6'-ethylene aminopyridine)-1H-pyrrole are reduced.

19 g of a light violet substance are obtained.
Fp: 23°–24° C.

EXAMPLE 9

2(3'-amino-6'-ethylene aminopyridine)-1H-1-methylpyrrole 60.75 g 2-(3'-nitro-6'-ethylene aminopyridine)-1H-1-methylpyrrole are reduced in an analogous manner with example 6.

24 g of a violet, oily substance are obtained. Fp of hydrochloride

Further variations and modifications of the foregoing will be apparent to those skilled in the art and are intended to be encompassed by the appended claims.

German priority applications P 37 31 396.7 and P 38 04 221.5 are incorporated herein by reference.

We claim:

1. A hair dye composition based on oxidation hair dyes which contain a developer component, coupling component and oxidation component, comprising as the coupling component at least one aminopyrrole derivative of the formula I

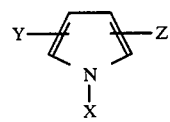

(I)

in which X represents hydrogen, a methyl or ethyl group, Y is in position 4 or 5 in the ring and represents hydrogen, an amino, hydroxy or methyl group, an alkoxy group with 1 to 3 C atoms or Y represents a second group Z, and Z stands in position 2 or 3 in the ring and represents a group of the general formula II $$-(C_nH_{2n})-NH-R \qquad (II)$$

in which n represents a number from 1 to 3 and R represents an N-methylpyrrole or N-ethylpyrrole, pyrrole, pyridine, piperidine, pyrimidine or morpholine group which is unsubstituted or amine-, methoxy- or ethoxy- or amine- and methoxy- or ethoxy-substituted at any position.

2. The hair dye composition according to claim 1, which contains other coupling components in addition to the alkylaminopyrrole derivative.

3. The compound 2-(5'-amino-2'-methoxy-6'-ethylene aminopyridine)-1H-pyrrole.

4. The compound 2-(5'-amino-2'-methoxy-6'-ethylene aminopyridine)-1H-1-methyl-pyrrole.

5. The compound 2-(3'-amino-6'-ethylene aminopyridine)-1H-pyrrole.

6. The compound 2-(3'amino-6'-ethylene aminopyridine)-1H-1 methyl-pyrrole.

7. The hair dye composition according to claim 1 in the form of a cream, emulsion or gel.

8. A hair dye composition containing the compound according to claim 3.

9. A hair dye composition containing the compound according to claim 4.

10. A hair dye composition containing the compound according to claim 5.

11. A hair dye composition containing the compound according to claim 6.

* * * * *